United States Patent [19]

Holter

[11] 4,433,181

[45] Feb. 21, 1984

[54] PROCESS FOR RECOVERING A CRYSTALLIZATION MEDIUM

[75] Inventor: Samuel N. Holter, Pittsburgh, Pa.

[73] Assignee: Koppers Company, Inc., Pittsburgh, Pa.

[21] Appl. No.: 343,537

[22] Filed: Jan. 28, 1982

Related U.S. Application Data

[63] Continuation-in-part of Ser. No. 158,995, Jun. 12, 1980, abandoned.

[51] Int. Cl.³ ............................................. C07C 37/84
[52] U.S. Cl. ................................... 568/750; 568/751; 568/756
[58] Field of Search ........................ 568/750, 751, 756

[56] References Cited

U.S. PATENT DOCUMENTS

| | | | |
|---|---|---|---|
| 2,493,781 | 1/1950 | Schneider et al. | 568/756 |
| 2,499,236 | 2/1950 | Gilder et al. | 568/756 |
| 2,536,040 | 1/1951 | Davidson | 568/756 |
| 2,863,927 | 12/1958 | Parisse | 568/750 |

FOREIGN PATENT DOCUMENTS

| | | | |
|---|---|---|---|
| 1145628 | 3/1963 | Fed. Rep. of Germany | 568/780 |
| 1223066 | 7/1973 | United Kingdom | 568/756 |

*Primary Examiner*—Werren B. Lone
*Attorney, Agent, or Firm*—Donald M. MacKay; Herbert J. Zeh, Jr.

[57] ABSTRACT

A process is provided for recovering the crystallization medium used for separating a 2,6-disubstituted phenol (DSP) from a feedstock containing it and a phenol in which only one of the 2 or 6 carbon positions are substituted (MSP). More particularly, the process comprises crystallizing said DSP from said feedstock with a water miscible non solvent crystallization medium, separating the resultant DSP crystals from said crystallization medium and feedstock, washing said DSP crystals with crystallization medium, washing said DSP crystals with water, passing the aforesaid wash water and crystallization medium along with the crystallization medium and feedstock from which the DSP was crystallized to an extraction means and extracting MSP with a water immiscible and crystallization medium immiscible extractant, stripping the extractant from the MSP and recycling the extractant to the extraction means and separating water from the crystallization medium of the extraction means and recycling the water for use in the water wash or extraction means and recycling the crystallization medium for the initial crystallization, the wash of the DSP crystals, or to the extraction means.

10 Claims, 1 Drawing Figure

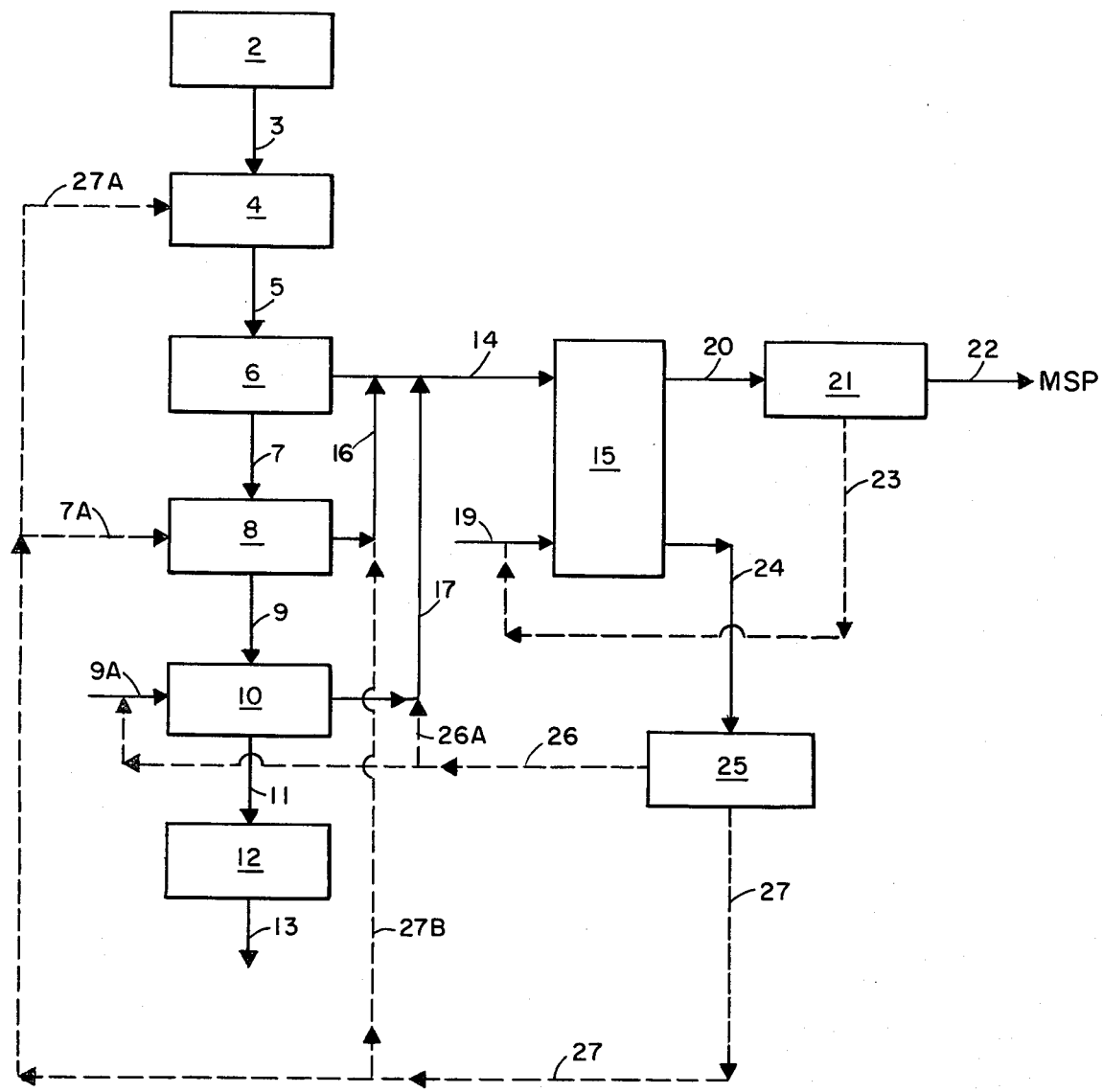

PROCESS FOR RECOVERING A CRYSTALLIZATION MEDIUM

CROSS REFERENCE TO RELATED APPLICATION

This is a continuation in part of U.S. Ser. No. 06,158,995 filed June 12, 1980, now abandoned.

BRIEF SUMMARY OF THE INVENTION

A process is provided for recovering the crystallization medium used for separating a 2,6-disubstituted phenol (DSP) from a feedstock containing it and a phenol in which only one of the 2 or 6 carbon positions is substituted (MSP). More particularly, the process comprises crystallizing said DSP from said feedstock with a water miscible non solvent crystallization medium, separating the resultant DSP crystals from said crystallization medium and feedstock, washing said DSP crystals with crystallization medium, washing said DSP crystals with water, passing the aforesaid wash water and crystallization medium along with the crystallization medium and feedstock from which the DSP was crystallized to an extraction means and extracting MSP with a water immiscible and crystallization medium immiscible extractant, stripping the extractant from the MSP and recycling the extractant to the extraction means and separating water from the crystallization medium of the extraction means and recycling the water for use in the water wash or extraction means and recycling the crystallization medium for the initial crystallization, the wash of the DSP crystals, or to the extraction means.

BACKGROUND OF THE INVENTION

In the alkylation of phenols to form 2,6-disubstituted phenols, byproducts are formed such as phenols in which only one of the 2 or 6 carbon positions are substituted. The recovery of the 2,6-disubstituted phenol, di-tertiary-butyl-para-cresol, from various crude products containing related chemical compounds such as mono-tertiary-butyl-para-cresol is illustrated in U.S. Pat. No. 2,863,927 to Parisse and assigned to Koppers Company, Inc. In recovering the DSP crystals, a substantial amount of crystallization medium, extractant and wash water must be disposed of. The present invention provides a means for continuously recycling these liquids after removing substantially all of the impurities. Thus the invention provides a means for lowering the cost of the process while reducing or eliminating the emission of noxious chemicals to the environment.

BRIEF DESCRIPTION OF THE DRAWING

The drawing is a flow diagram of the process of the invention.

DETAILED DESCRIPTION OF THE INVENTION

Referring now to the drawing, an alkylation feedstock 2 is passed via conduit 3 to a crystallization zone 4. Typical feedstocks may contain 2,6-di-tertiary-butyl-phenol and 2,4-di-tertiary-butyl-phenol; 2,6-xylenol with ortho-, meta- and para-cresol; and 2,6-di-normal-butyl-para-cresol and 4,6-normal-dibutyl-meta-cresol. The crystallization medium is a water miscible non solvent for the DSP. Typical materials include glycols such as ethylene and propylene glycol, diethylene glycol and 2,3-butanediol; glycerin, amides such as propionamde, dimethylformamide, dimethylacetamide, formamide, and methylformamide; lower aliphatic alcohols such as methanol, ethanol, n-propanol and isopropanol; unsaturated alcohols such as allyl alcohol and propargyl alcohol; glycol ethers such as ethylene glycol monomethyl ether and ethylene glycol dimethyl ether; aliphatic acids such as formic, acetic and propionic; nitriles such as acetonitrile; cyclic ethers such as tetrahydrofuran and 1,4-dioxane; ketones such as acetone and butanone; lactones such as propiolactone and butyrolactone, and miscellaneous compounds such as morpholine, nitromethane, pyridine and sulfolane. The above compounds can be used alone, with water or as mixtures of compounds with or without water, depending upon the particular compound employed. The mixture of crystallization medium and feedstock is typically heated to about 80° C. to form a solution and thereafter cooled to about 15° C. wherein substantially all of the DSP crystallizes out. The mixture is passed via conduit 5 to a separation zone 6 where the DSP crystals may be recovered by filtration or centrifugation. The crystals are then passed via conduit 7 to be washed with the crystallization medium such as a glycol and then passed via conduit 9 to a water wash 10 and ultimately to drying zone 12 via conduit 11 where the crystals are dried to a constant weight such as in a vacuum oven at 50° C. The separation medium 6 containing crystallization medium and aqueous feedstock is passed via conduit 14 to extraction zone 15 wherein the MSP and extractant introduced from conduit 19 are removed via conduit 20 and the extractant stripped from the MSP in zone 21 and the MSP discarded via conduit 22 or further processed to remove impurities. The extractant is a water immiscible and crystallization medium immiscible material. Typical materials include aliphatic and aromatic hydrocarbons which may be halo substituted. Typical aliphatics include hexane, octane, pentane, decane, cyclohexane, petroleum ether, ligroin, diisobutylene, triisobutylene, kerosene, gasoline, or even butane or propane (under light pressure such as about 110 psig at 21° C.). Typical aromatics include benzene, toluene, ethylbenzene, tetralin and xylene. Typical halogenated derivitives include 1,2-dichloroethane, butyl chloride, chloroform, trichloroethylene, tetrachloroethane, bromobenzene, carbon tetrachoride and chlorobenzene. Other suitable extractants include ethers such as diethyl ether, dipropyl ether, dibutyl ether, anisole and methyl t-butyl ether; esters such as ethyl acetate, butyl acetate, amyl acetate and ethyl benzoate; higher aliphatic alcohols such as ethyl hexanol and miscellaneous compounds such as dimethyl sulfide, carbon disulfide, thiophene, benzonitrile, nitrobenzene and acetophenone. Preferably the extractant will not dissolve more than about 0.1% of the crystallization medium. The extraction can be conducted at a temperature between about 0° C. and about 100° C. and at a pressure between about atmospheric and about 500 psig, depending upon the materials employed. Similarly, the stripping of the extractant can be conducted at a temperature between about 25° C. and about 98° C. and at a pressure between about 0.87 psig and about atmospheric, depending upon the constituents of the feedstock. The extraction medium from stripping zone 21 is passed via conduit 23 to be mixed with extractant added to extraction zone 15 via conduit 19. The crystallization medium from extraction zone 15 is removed via conduit 24 and passed to a separation zone 25 wherein the water and crystallization medium are separated. The water may be removed such as by flash vaporization at a temperature between about 25° C. and about 100° C. and a pressure between about 0.77 psig and about atmospheric, and passed via conduit 26 to be recycled to water wash zone 10 and ultimately to extraction zone 15, or directly via conduit 26A to extraction zone 15. The crystallization medium from separation zone 25 is passed via conduit 27 to be employed in wash zone 8, or passed via conduit 27A to crystallization zone 4.

The following examples will serve to illustrate the invention. All parts and percentages in said examples and elsewhere in the specification and claims are by weight unless otherwise specified.

EXAMPLES

An alkylation feedstock containing 2,6-ditert-butyl-p-cresol and 2,4-ditert-butyl-m-cresol was fed to a crystallization zone 4 via conduit 3. A crystallization medium of 85% propylene glycol and 15% water was employed at a 3:1 proportion with the feedstock. The mixture was vigorously stirred while heating to 80° C. and then cooled to 15° C. to crystallize the 2,6-ditert-butyl-p-cresol (DTBPC). The mixture was then passed to a filtration or centrifugation separation zone 6 via conduit 5 where the DTBPC crystals were separated. The crystals were first passed to wash zone 8 via conduit 7 where the impurities were removed with propylene glycol, and then to water wash zone 10 via conduit 9 to remove any water soluble impurities. The purified crystals were then passed to drying zone 12 via conduit 11 where the crystals were dried to constant weight in a vacuum oven at a temperature of 50° C., and recovered via conduit 13. The mother liquor from separation medium 6 was passed to extraction zone 15 via conduit 14 along with glycol wash via conduit 16 and water wash via conduit 17. Heptane, the glycol extraction medium, was added via conduit 19 in a ratio of heptane to mother liquor of from 1:1 to 3:1 and removed via conduit 20 to be distilled in stripping zone 21. The stripping zone was maintained at 45 torr and a maximum bath temperature of 80° C. with the aid of a Buchi rotary evaporator to remove the more volatile heptane extractant via conduit 23 and recycled via conduit 19 to extraction zone 15.

The residue comprising 2,4-ditert-butyl-m-cresol was removed via conduit 22 to be disposed of or further processed to separate any contaminants. The aqueous glycol mixture was passed from extraction zone 15 to flash evaporator 25 via conduit 24, wherein water was removed via conduit 26 for recycle to water wash zone 10 and glycol was recycled via conduit 27 to glycol wash zone 8. The water was removed from the glycol-water phase at ca. 45 torr and maximum bath temperature of 80° C. with the aid of a Buchi rotary evaporator.

The above procedure was repeated employing other crystallization media to include glycerin, formamide, diethylene glycol and a 1:1 ethylene glycol/propylene glycol mixture. The highest yields of high purity product were obtained with from 5–15% water and 95–85% propylene glycol, as shown in the following Table I.

In addition, DTBPC was separated from other feedstocks. The Acid Alkylate comprised DTBPC and mono-t-butyl-p-cresol (MTBPC) and mono-t-butyl-m-cresol (MTBMC) and di-t-butyl-m-cresol (DTBMC). The Mono Overhead was distillate from removal of mono butylated cresols and comprised DTBPC, MTBPC, and MTBMC; the CC Oil was the residual oils from crystallization and centrifugation of crude DTBPC and comprised DTBPC, MTBPC, and MTBMC; GX-3 was from crude distilled DTBPC and comprised DTBPC, MTBPC, and MTBMC; and F.P. is the freezing point.

TABLE I

| | DTBPC YIELDS FROM VARIOUS MEDIA | | | | |
|---|---|---|---|---|---|
| Example No. | Medium | Solubility Parameter,[1] $\delta$ | Medium/ Feedstock | F.P., °C. | Purity, % | Yield, % |
| | A. Acid Alkylate | | | | | |
| 2 | Propylene Glycol (PG) | 12.6 | 3:1 | 68.5 | 97.81 | 53.6 |
| 3 | PG-H$_2$O (95/5) | (13.2)[2] | 3:1 | 68.3 | 97.48 | 65.2 |
| 4 | PG-H$_2$O (85/15) | (14.3)[2] | 3:1 | 68.2 | 97.31 | 71.3 |
| 5 | PG-H$_2$O (75/25) | (15.4)[2] | 3:1 | 67.1 | 95.48 | 61.9 |
| 6 | Glycerin | 16.5 | 3:1 | 66.3 | 94.15 | 23.6 |
| 7 | Formamide | 19.2 | 3:1 | 66.0 | 93.65 | 33.2 |
| | B. Mono Overhead | | | | | |
| 8 | PG | 12.6 | 3:1 | 66.9 | 95.15 | 32.2 |
| 9 | PG-H$_2$O (85/15) | (14.3)[2] | 3:1 | 66.8 | 94.98 | 56.8 |
| | C. CC Oil | | | | | |
| 10 | Diethylene Glycol | 12.1 | 4:1 | 68.0 | 96.98 | 69.6 |
| 11 | PG | 12.6 | 1:1 | 66.9 | 95.15 | 85.9 |
| 12 | EG/PG (1:1) | (13.6)[2] | 1:1 | <65.0 | <92.00 | <88.4 |
| 13 | PG-H$_2$O (85/15) | (14.3)[2] | 3:1 | 67.8 | 96.64 | 87.2 |
| 14 | Glycerin | 16.5 | 1:1 | 65.2 | 92.33 | 79.7 |
| 15 | Formamide | 19.2 | 1:1 | 67.7 | 96.48 | 82.4 |
| | D. GX-3 | | | | | |
| 16 | PG | 12.6 | 1:1 | 68.4 | 97.64 | 94.9 |
| 17 | EG/PG (1:1) | (13.6)[2] | 1:1 | 67.4 | 95.98 | 95.9 |

[1] Burrell H., Polymer Handbook 2nd Ed.
[2] Calculated using $\delta = \phi_1 \delta_1 + \phi_2 \delta_2$ From the data reported in Table I, it can be seen that propylene glycol appeared to give a higher yield of DTBPC with higher purity than did the other cyrstallization media. Although a 1:1 ethylene glycol/propylene glycol mixture gave a higher yield, the purity was lower. Formamide gave a good yield of DTBPC with purity comparable to that obtained with propylene glycol. At a 3:1 glycol/feedstock ratio, a propylene glycol/water mixture of 85%/15% afforded the highest yield of DTBPC and is the preferred crystallization medium.

The effect of increasing the proportion of crystallization medium to feedstock was determined with CC oil and acid alkylate as feedstocks, as shown in the following Table II.

TABLE II
DTBPC YIELDS AT VARIOUS CRYSTALLIZATION MEDIUM/FEEDSTOCK RATIOS

| Example No. | Medium | Feedstock | Medium/ Feedstock | F.P., °C. | Purity, % | Yield, % |
|---|---|---|---|---|---|---|
| 18 | PG | CC oil | 1:1 | 68.2 | 97.31 | 81.5 |
|  |  |  | 3:1 | 68.7 | 98.14 | 81.3 |
|  |  |  | 5:1 | 68.4 | 97.64 | 68.4 |
|  |  |  | 10:1 | 68.1 | 97.14 | 60.7 |
| 19 | Glycerin | CC oil | 1:1 | 68.3 | 97.48 | 78.6 |
|  |  |  | 3:1 | 68.3 | 97.48 | 77.4 |
|  |  |  | 5:1 | 68.8 | 98.31 | 75.2 |
| 20 | Formamide | CC oil | 1:1 | 67.7 | 96.48 | 82.4 |
|  |  |  | 3:1 | 68.1 | 97.14 | 89.7 |
|  |  |  | 5:1 | 67.9 | 96.81 | 84.5 |
| 21 | PG | Acid alkylate | 1:1 | 69.4 | 99.30 | 54.1 |
|  |  |  | 3:1 | 69.3 | 99.14 | 58.5 |
|  |  |  | 5:1 | 68.5 | 97.81 | 56.3 |
|  |  |  | 10:1 | 68.8 | 98.31 | 37.8 |

From the data reported in Table II it can be seen that at PG/CC oil ratios greater than 3:1, the yield decreases substantially. With glycerin, the yield, although lower, did not change as dramatically as with PG-78.6% at 1:1 down to 75.2% at 5:1 versus 81.5% down to 68.4% with PG. The purity of DTBPC remained fairly constant regardless of the ratio used.

Formamide with CC oil gave higher yields of DTBPC than did the previous media, 82-89% compared to 75-78% with glycerin or 68-81% with PG, although the purity of product was slightly lower.

Finally, the effect on yield of increasing amounts of PG with acid alkylate was determined. The yield appeared to peak at 3:1 PG/acid alkylate and then decrease to 37.8% at a 10:1 ratio. The purity at 1:1 and 3:1 ratios was greater than 99%. Product yield and purity from CC oil did not vary appreciably as the proportion of crystallization medium was increased, except for PG at 5:1.

Acid alkylate and CC oil were used as feedstocks and yield of DTBPC determined as a function of crystalization temperature as shown in the following Table III.

TABLE III
DTBPC YEILD AS A FUNCTION OF TEMPERATURE

| Example No. | Feedstock | PG/ Feedstock | Temp., °C. | F.P., °C. | Purity, % | Yield, % |
|---|---|---|---|---|---|---|
| 22 | Acid alkylate | 3:1 | 37 | — | — | <23.4 |
|  |  |  | 15 | — | — | <25.7 |
|  |  |  | 5 | 69.2 | 98.97 | 58.5 |
| 23 | Acid alkylate |  | −15 | 68.3 | 97.48 | 61.4 |
| 24 | CC oil | 1:1 | 20 | 66.8 | 94.98 | 83.1 |
|  |  |  | 15 | 66.4 | 94.32 | 83.5 |
| 25 | CC oil | 3:1 | 25 | 67.3 | 95.81 | 80.8 |
|  |  |  | 20 | 67.5 | 96.15 | 81.8 |
|  |  |  | 15 | 67.7 | 96.48 | 82.3 |
| 26 | CC oil | 3:1 | 25 | 67.2 | 95.65 | 77.2 |

From the data it can be seen that with a 3:1 PG/acid alkylate ratio, the yield of DTBPC increased from less than 23% at a final crystallization temperature of 37° C. to 61% at a temperature of −15° C. A repeat experiment at 15° C. and 3:1 PG/feedstock ratio afforded a DTBPC yield of 53%, which is not substantially lower than that obtained at 5° C. This suggests that there is no advantage in cooling the crystallization mixture below 15° C., since refrigeration costs would offset the slight increase in DTBPC yield.

The variation in yield with respect to ultimate crystallization temperature was not as large with CC oil as with acid alkylate. A decrease of 5° C. appeared to increase the yield of DTBPC by about 0.6% at 1:1 PG/CC oil. At a 3:1 PG/CC oil ratio, a decrease in temperature from 25° C. to 20° C. to 15° C. only increased the yield by 1.5%. while the product purity varied from 95.8 to 96.5%.

In addition to heptane, the mother liquor was extracted with diisobutylene and water. Heptane extracted about 25%, diisobutylene about 20%, and water effected a separation of about 50% of the estimated phenolic content of the mother liquor when extracted once with a 3:1 liquor/extractant ratio.

Equal weights of propylene glycol mother liquor (3:1 PG/acid alkylate crystallization) were extracted one time with successively higher proportions by weight of heptane, namely 3:1, 1.5:1 and 1:1. The DTBPC content of the mother liquor (ca.4.1%) was reduced to 1.4, 1.1 and 0.7%, respectively, in the raffinate. Moreover, the PG content of the heptane phase was less than 0.5%.

The effect of multiple extractions with heptane on a PG/acid alkylate mother liquor was determined. Three extractions with an equal weight of heptane reduced the DTBPC content of the mother liquor to ca.0.1%. Total residual phenolics amounted to about 1.5% with MTBMC and DTBMC as the major components. These results show that a major portion of the phenolic components can be recovered by extraction.

To recover the glycol, the mother liquor from crystallization of DTBPC from acid alkylate with PG (1:3) was combined with the centrifuge wash water. The aqueous glycol was then extracted with heptane followed by partial dehydration under 40-60 torr at a bath temperature of 55° C. The heptane was also stripped from the extract under similar conditions. As the results in Table IV indicate, separation of the process liquors is accomplished. By this procedure the phenolic content of the glycol was reduced to less than 1% and water to about 3%. Phenolics in recovered water were less than 300 ppm.

TABLE IV
ANALYSIS OF PHASES FROM GLYCOL RECOVERY

| Phase Component | Glycol Weight Percent | Water | Heptane |
|---|---|---|---|
|  |  | ppm by Weight | |
| DTBPC | 0.29 | 6 | 335 |
| Phenol/o-Cresol | 0.016 | 20 | — |
| m-/p-Cresol | 0.20 | 180 | — |
| MTBPC | 0.035 | 10 | 26 |
| MTBMC | 0.15 | 38 | 110 |
| PTBMC[1]/DTBMC | 0.20 | 7 | 385 |
| Unknowns (No.) | 0.06 (4) | 22 (3) | 120 (5) |
| Water | 3.1 | N.D.[2] | N.D.[2] |

[1]PTBMC is para-tertiary-butyl-meta-cresol.
[2]Not determined.

The feasibility of recycling glycol, water and heptane was determined and the effects on yield and purity measured. The materials recovered from the above experiment were used to crystallize DTBPC from acid alkylate and recycled three times. The yield and purity of the DTBPC did not appear to be affected.

Gas chromatographic analyses of recovered heptane, water, PG and residue from DTBPC crystallization of acid alkylate are given in the following Table V. These materials were recovered at 45 torr and 80° C. bath temperature.

TABLE V
ANALYSIS OF RECOVERED MATERIALS FROM DTBPC CRYSTALLIZATION[1]

| | | | | | | | | | Propylene | PTBMC/ |
|---|---|---|---|---|---|---|---|---|---|---|
| Example No. | DTBPC | Phenol | m-/p-Cresol | MTBPC | MTBMC | Unknowns | Water | Heptane | glycol | DTBMC/ |
| 27[2] | 0.002 | 0.013 | 0.18 | 0.19 | 0.058 | 0.074(4) | 5.9 | <0.5 | — | 0.079 |
| 28[2] | 0.003 | 0.012 | 0.17 | 0.56 | 0.15 | 0.080(5) | 5.7 | <0.5 | — | 0.102 |
| 29[2] | <0.001 | 0.011 | 0.15 | 0.48 | 0.15 | 0.099(4) | 7.1 | <0.5 | — | 0.073 |
| 30[3] | 0.001 | 0.003 | 0.017 | 0.017 | 0.006 | 0.003(4) | — | <0.5 | 3.5 | 0.002 |
| 31[3] | <0.001 | 0.003 | 0.017 | 0.008 | 0.003 | 0.003(3) | — | <0.5 | 5.0 | 0.001 |
| 32[3] | <0.001 | 0.003 | 0.014 | 0.010 | 0.004 | 0.004(3) | — | <0.5 | 3.9 | <0.001 |
| 33[4] | 19.3 | — | 2.5 | 1.4 | 4.9 | — | <1.0 | <1.0 | 4.8 | 44.4 |
| 34[4] | 19.9 | — | 1.6 | 2.9 | 9.6 | — | <1.0 | <1.0 | 7.7 | 41.0 |
| 35[4] | 20.1 | — | 1.6 | 3.0 | 10.0 | — | <1.0 | <1.0 | 6.7 | 38.7 |
| 36[5] | 0.091 | — | — | 0.033 | 0.011 | 0.027(6) | <0.1 | — | <0.05 | 0.052 |
| 37[5] | 0.090 | 0.011 | — | 0.057 | 0.017 | 0.016(7) | <0.1 | — | <0.05 | 0.035 |
| 38[5] | 0.060 | 0.007 | — | 0.041 | 0.013 | 0.010(7) | <0.1 | — | <0.05 | 0.022 |

[1]Stripped at 45 torr and 80° C. from 3:1 PG/acid alkylate.
[2]Recovered PG.
[3]Recovered water.
[4]Residue.
[5]Recovered heptane.

From the data it can be seen that no substantial increase in the phenolic content occurred in the PG or water phase upon repeated use. Water content of the glycol ranged from 5.7 to 7.1%. Recovery of the heptane afforded a residue containing about 20% DTBPC along with the other butylated cresols. About 5 to 7.7% PG was also present in the residue, but this can be reduced by increasing the amount of water added to the mother liquor. The recovered heptane was relatively free of impurities rendering it quite suitable for recycle, and the heptane recovery was about 95% while the recovery of PG, water and heptane residue totalled about 93%.

Since glycol was detected in the residues from the heptane extractions, experiments were conducted to determine the effect of increasing the amount of water added to the mother liquor. Mother liquors from crystallization of DTBPC from acid alkylate were combined with the aqueous centrifuge wash and additional water added to give the liquor/water ratios shown in Table VI.

TABLE VI
EFFECT OF WATER ADDITION TO GLYCOL MOTHER LIQUOR

| Example No. | Liquor/Water | Glycol in Heptane Residue, Weight Percent |
|---|---|---|
| 39 | 2.0/1 | 3.5 |
| 40 | 1.75/1 | 2.6 |
| 41 | 1.5/1 | 1.9 |

From the data reported in the Table it can be seen that an increase in the amount of water decreases the amount of glycol remaining in the heptane extraction residue.

What is claimed is:

1. A process to recover the crystallization medium for separating a 2,6-disubstituted phenol (DSP) from a feedstock containing it and a phenol in which only one of the 2 or 6 carbon positions is substituted (MSP), said process comprising:

(a) crystallizing said DSP from said feedstock with a water miscible, non solvent crystallization medium;
(b) separating the resultant DSP crystals from said crystallization medium and feedstock;
(c) washing said DSP crystals with crystallization medium;
(d) washing said DSP crystals with water;
(e) passing the wash water from (d) and the crystallization medium from (c) along with the crystallization medium and feedstock of (b) to an extraction means and extracting MSP with a water imiscible and crystallization medium immiscible extractant;
(f) stripping the extractant from the MSP of (e) and recycling the extractant for use in step (e); and
(g) separating water from the crystallization medium of step (e) and recycling the water for use in step (d) or (e) and recycling the crystallization medium for use in step (a), (c) or (e).

2. The process of claim 1 wherein the 2,6-disubstituted phenol is ditertiary-butyl-para-cresol.

3. The process of claim 1 wherein the MSP phenol is 2,4-ditertiary-butyl-phenol.

4. The process of claim 1 wherein the crystallization medium is selected from glycols, glycerin, formamide, methylformamide, and mixtures.

5. The process of claim 1 wherein the ratio of crystallization medium to feedstock is from between about 1:1 to 3:1.

6. The process of claims 1 or 5 wherein the crystallization medium comprises from 95 to 85% propylene glycol and 5 to 15% water.

7. The process of claim 1 wherein the extractant is an aliphatic or aromatic hydrocarbon which may be halo substituted.

8. The process of claim 1 wherein the extractant is heptane or diisobutylene.

9. The process of claim 1 wherein the crystallization medium comprises from 95 to 85% propylene glycol and 5 to 15% water in a ratio of crystallization medium to feedstock of about 3:1.

10. The process of claim 1 wherein the nonaqueous feedstock and crystallization medium to water ratio in the extraction means is about 1.5:1 or less.

* * * * *